(12) United States Patent
Selnick et al.

(10) Patent No.: US 8,796,260 B2
(45) Date of Patent: Aug. 5, 2014

(54) IMIDAZOBENZAZEPINE CGRP RECEPTOR ANTAGONISTS

(75) Inventors: Howard G. Selnick, Ambler, PA (US); Ian M. Bell, Harleysville, PA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 422 days.

(21) Appl. No.: 12/867,332

(22) PCT Filed: Feb. 6, 2009

(86) PCT No.: PCT/US2009/033288
§ 371 (c)(1), (2), (4) Date: Aug. 12, 2010

(87) PCT Pub. No.: WO2009/105348
PCT Pub. Date: Aug. 27, 2009

(65) Prior Publication Data
US 2010/0324023 A1    Dec. 23, 2010

Related U.S. Application Data

(60) Provisional application No. 61/066,194, filed on Feb. 19, 2008.

(51) Int. Cl.
*A61K 31/55* (2006.01)
*C07D 487/12* (2006.01)

(52) U.S. Cl.
USPC ............ 514/214.02; 540/578; 540/579

(58) Field of Classification Search
USPC ............... 514/214.02; 540/578, 579
See application file for complete search history.

(56) References Cited

U.S. PATENT DOCUMENTS

| | | |
|---|---|---|
| 6,476,020 B1 | 11/2002 | Liu et al. |
| 6,953,790 B2 | 10/2005 | Burgey et al. |
| 7,235,545 B2 | 6/2007 | Burgey et al. |
| 7,390,798 B2 | 6/2008 | Williams et al. |
| 7,452,903 B2 | 11/2008 | Burgey et al. |
| 7,491,713 B2 | 2/2009 | Burgey et al. |
| 7,534,784 B2 | 5/2009 | Burgey et al. |
| 7,629,338 B2 | 12/2009 | Wood et al. |
| 7,659,264 B2 | 2/2010 | Burgey et al. |
| 7,745,427 B2 | 6/2010 | Paone et al. |
| 7,772,224 B2 | 8/2010 | Paone et al. |
| 7,893,052 B2 | 2/2011 | Paone et al. |
| 8,003,792 B2 | 8/2011 | Bell et al. |
| 2006/0094707 A1 | 5/2006 | Chaturvedula et al. |
| 2006/0229447 A1 | 10/2006 | Chaturvedula et al. |
| 2007/0259850 A1 | 11/2007 | Mercer et al. |
| 2007/0259851 A1 | 11/2007 | Chaturvedula et al. |
| 2007/0265225 A1 | 11/2007 | Wood et al. |
| 2008/0113966 A1 | 5/2008 | Burgey et al. |

FOREIGN PATENT DOCUMENTS

| | | |
|---|---|---|
| WO | 2004092166 A2 | 10/2004 |
| WO | 2006031606 A2 | 3/2006 |
| WO | 2006052378 A2 | 5/2006 |
| WO | 2007131020 A2 | 11/2007 |
| WO | 2006044504 A2 | 5/2010 |

OTHER PUBLICATIONS

Supplementary European Search Report dated (Jul. 12, 2011), for related European Application No. EP09 71 2273; 5 pages.

*Primary Examiner* — Brenda Coleman
(74) *Attorney, Agent, or Firm* — H. Eric Fischer; John C. Todaro

(57) ABSTRACT

Compounds of Formula I: I (where variables $R^{1A}$, $R^{1B}$, $R^2$, $R^3$, $R^4$, A, and Z are as defined herein) useful as antagonists of CGRP receptors, and useful in the treatment or prevention of diseases in which CGRP receptors are involved, such as headache, and in particular migraine and cluster headache. The invention is also directed to pharmaceutical compositions comprising these compounds and the use of these compounds and compositions in the prevention or treatment of such diseases in which CGRP receptors are involved.

(I)

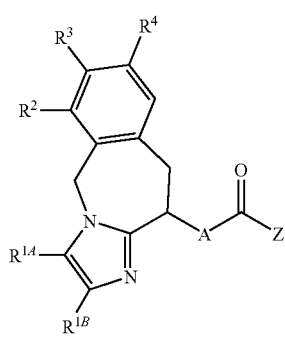

12 Claims, No Drawings

IMIDAZOBENZAZEPINE CGRP RECEPTOR ANTAGONISTS

This application is a national stage application filed under 35 U.S.C. 371 of PCT/US09/33288, filed Feb. 6, 2009 which claims benefit of U.S. Provisional Application No. 61/066,194, filed Feb. 19, 2008.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine. CGRP ([Cys(ACM)2,7] CGRP), is a selective agonist of $CGRP_2$. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), salivary levels of CGRP are elevated in migraine subjects between attacks (Bellamy et al., Headache, 2006, 46, 24-33), and CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis, Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist B1BN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin hives Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sei., 1992, 657, 397-404; Schini et al, Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to imidazobenzazepine compounds of Formula I:

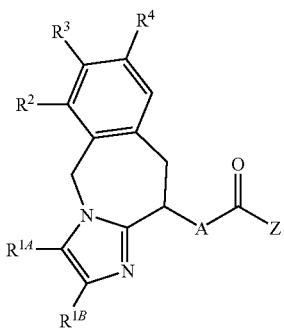

(where variables $R^{1A}$, $R^{1B}$, $R^2$, $R^3$, $R^4$, A, and Z are as defined herein) useful as antagonists of CGRP receptors, and useful in the treatment or prevention of diseases in which CGRP receptors are involved, such as headache, and in particular migraine and cluster headache. The invention is also directed to pharmaceutical compositions comprising these compounds and the use of these compounds and compositions in the prevention or treatment of such diseases in which CGRP receptors are involved.

DETAILED DESCRIPTION OF THE INVENTION

The present invention is directed to imidazobenzazepine compounds of Formula I:

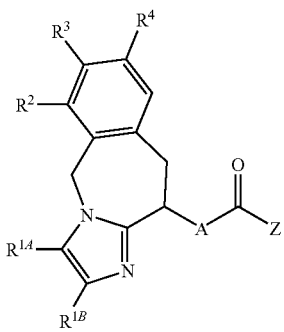

wherein:
A is $NR^5$ or $C(R^5)_2$;
Z is selected from:

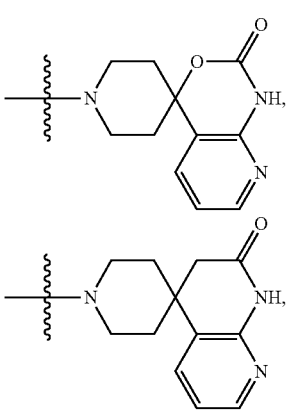

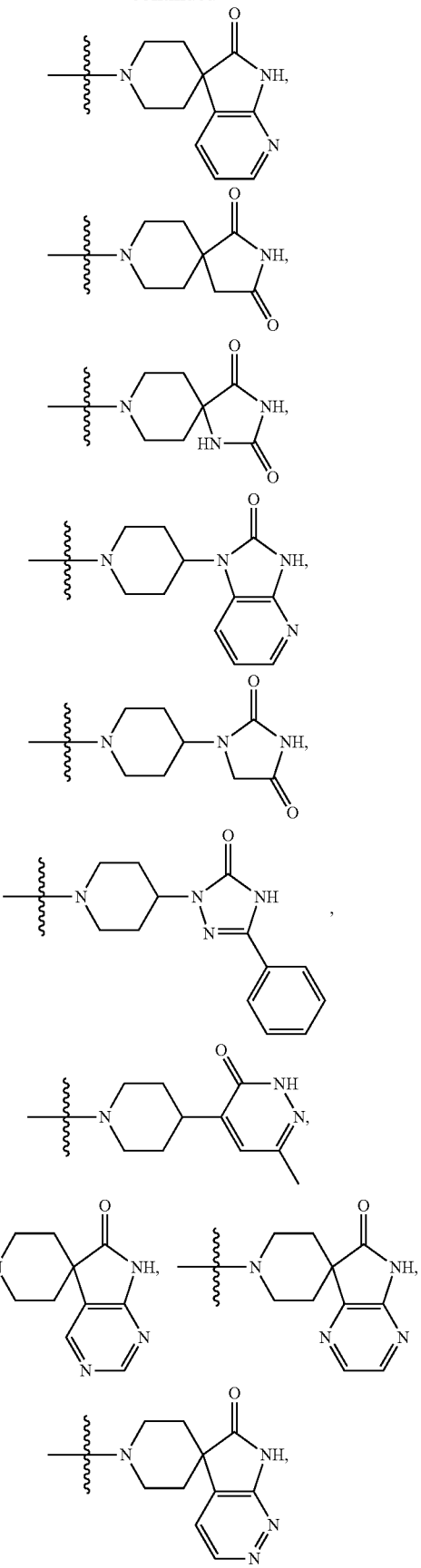

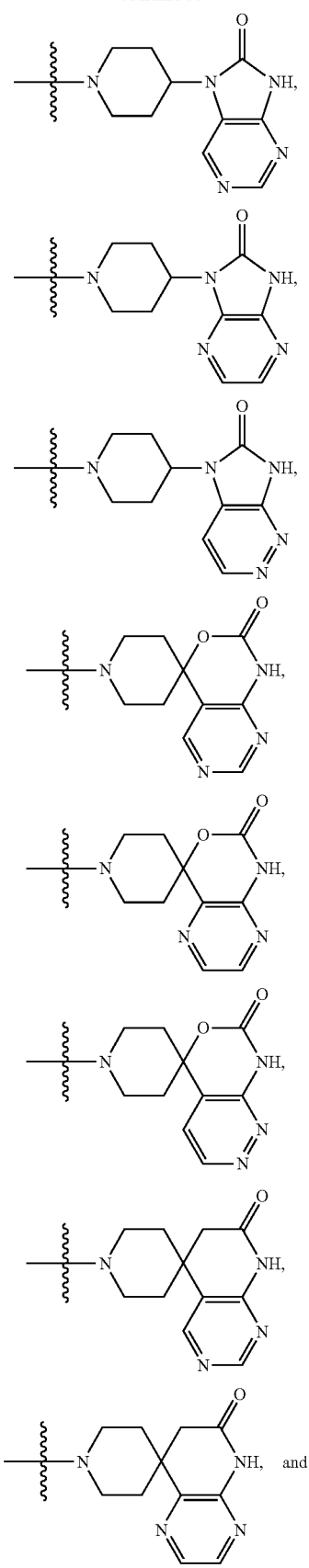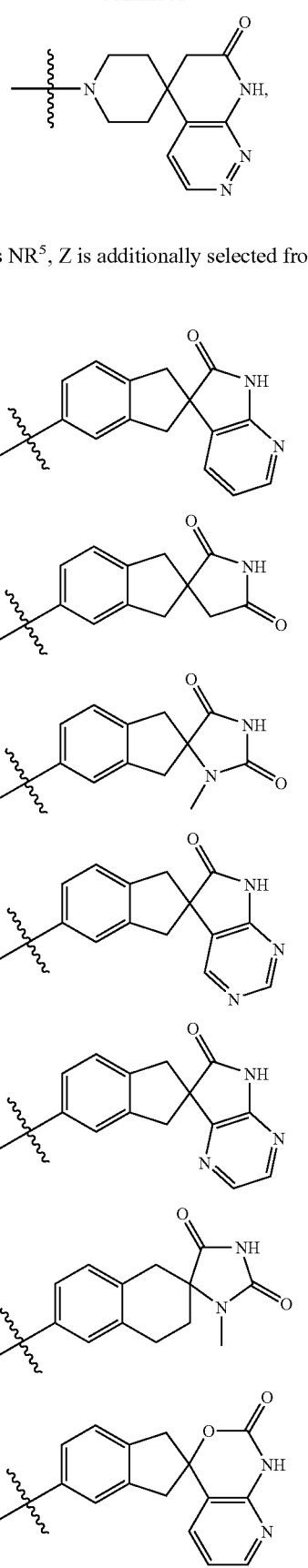
and when A is NR⁵, Z is additionally selected from:

-continued

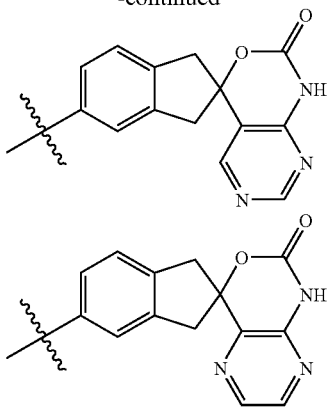

$R^{1A}$ and $R^{1B}$ are independently selected from:
1) H, $C_1$-$C_6$ alkyl, $C_{3-6}$ cycloalkyl and heterocycle, wherein said alkyl, cycloalkyl and heterocycle is optionally substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^5$,
   d) heteroaryl, unsubstituted or substituted with 1-5 substituents each independently selected from $R^5$,
   e) heterocycle, unsubstituted or substituted with 1-5 substituents each independently selected from $R^5$,
   f) $(F)_p C_{1-3}$ alkyl,
   g) halogen,
   h) $OR^5$,
   i) $O(CH_2)_s OR^5$,
   j) $CO_2 R^5$,
   k) CN,
   l) $NR^{10}R^{11}$, and
   mm) $O(CO)R^5$; and
2) aryl or heteroaryl, wherein said aryl or heteroaryl is optionally substituted with one or more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^5$,
   f) $CO_2 R^5$,
   g) $(CO)NR^{10}R^{11}$,
   h) $SO_2 NR^{10}R^{11}$,
   i) $N(R^{10})SO_2 R^{11}$,
   j) $S(O)_m R^5$,
   k) CN,
   l) $NR^{10}R^{11}$, and
   m) $O(CO)R^4$;

$R^2$ is hydrogen, halo, hydroxy, $C_{1-6}$alkyl, $C_{2-6}$alkenyl, or $NR^{10}R^{11}$;
$R^3$ is hydrogen, hydroxy, halo, $C_{1-6}$alkyl, or $C_{2-6}$alkenyl;
or $R^2$ and $R^3$ are linked together to form —C(H)=N—N($R^9$)— thereby forming a fused ring;
$R^4$ is hydrogen, halo, $C_{1-6}$alkyl, or $C_{2-6}$alkenyl;
$R^5$ is selected from: H, $C_{1-6}$ alkyl, $C_{3-6}$ cycloalkyl, aryl, heteroaryl and benzyl, wherein said alkyl, cycloalkyl, aryl or heteroaryl moiety is optionally substituted with halogen, hydroxy or $C_1$-$C_6$ alkoxy;

$R^{10}$ and $R^{11}$ are independently selected from: H, $C_{1-6}$ alkyl, $C_{3-6}$ cycloalkyl, aryl, heteroaryl and benzyl, wherein said alkyl, cycloalkyl, aryl or heteroaryl moiety is optionally substituted with halogen, hydroxy or $C_1$-$C_6$ alkoxy, provided that when $R^{10}$ and $R^{11}$ are bonded to the same nitrogen atom, then $R^{10}$ and $R^{11}$ and the nitrogen to which they are both attached form a ring selected from: azetidinyl, pyrrolidinyl, piperidinyl, piperazinyl and morpholinyl, which ring is unsubstituted or substituted with 1-5 substituents each independently selected from $R^5$;
p is 0 to 2q+1, for a substituent with q carbons
m is 0 to 2;
s is 1 to 3;
and pharmaceutically acceptable salts and individual stereoisomers thereof.

In some embodiments of the compounds of formula (I), $R^{1B}$ is hydrogen, and $R^{1A}$ is selected from:
1) H, $C_1$-$C_6$ alkyl, $C_{3-6}$ cycloalkyl and heterocycle, wherein said alkyl, cycloalkyl and heterocycle is optionally substituted with one or more substituents each independently selected from:
   a) $C_{1-6}$ alkyl,
   b) $C_{3-6}$ cycloalkyl,
   c) phenyl, unsubstituted or substituted with 1-5 substituents each independently selected from $R^5$,
   d) heteroaryl, unsubstituted or substituted with 1-5 substituents each independently selected from $R^5$, and where heteroaryl is selected from: imidazole, isoxazole, oxazole, pyrazine, pyrazole, pyridazine, pyridine, pyrimidine, and thiazole;
   e) heterocycle, unsubstituted or substituted with 1-5 substituents each independently selected from $R^5$, and where heterocycle is selected from: azetidine, dioxane, dioxolane, morpholine, oxetane, piperazine, piperidine, pyrrolidine, tetrahydrofuran, and tetrahydropyran;
   f) $_p C_{1-3}$ alkyl,
   g) halogen,
   h) $OR^5$,
   i) $O(CH_2)_s OR^5$,
   j) $CO_2 R^5$,
   k) CN,
   l) $NR^{10}R^{11}$,
   m) $O(CO)R^5$;
2) aryl or heteroaryl, selected from: phenyl, imidazole, isoxazole, oxazole, pyrazine, pyrazole, pyridazine, pyridine, pyrimidine, and thiazole, wherein said aryl or heteroaryl is optionally substituted with one or more substituents each independently selected from:
   a) $C_{1-6}$ alkyl,
   b) $C_{3-6}$ cycloalkyl,
   c) $(F)_p C_{1-3}$ alkyl,
   d) halogen,
   e) $OR^5$,
   f) $CO_2 R^5$,
   g) $(CO)NR^{10}R^{11}$,
   h) $SO_2 NR^{10}R^{11}$,
   i) $N(R^{10})SO_2 R^{11}$,
   j) $S(O)_m R^5$,
   k) CN,
   l) $NR^{10}R^{11}$, and
   m) $O(CO)R^5$.

In certain embodiments of the compounds of formula (I), $R^{1B}$ is hydrogen, and $R^{1A}$ is $C_1$-$C_6$ alkyl or $C_{3-6}$ cycloalkyl, optionally substituted with one or more substituents each independently selected from:
   a) $C_{1-6}$ alkyl,
   b) halogen, c) OH, d) $OC_{1-6}$ alkyl, and e) $NR^{10}R^{11}$ (for example, $NH_2$).

In certain embodiments, $R^2$ and $R^3$ are linked together to form —C(H)=N—N($R^9$)— thereby forming a fused ring.

In certain embodiments of the compounds of formula (I), $R^4$ is selected from: H, $C_{1-6}$ alkyl, or halogen, wherein said alkyl is optionally substituted with halogen, hydroxy or $C_1$-$C_6$ alkoxy.

In certain embodiments of the compounds of formula (I), A is —$CH_2$—. In other embodiments, A is —NH—.

In certain embodiments of the compounds of formula (I), Z is selected from:

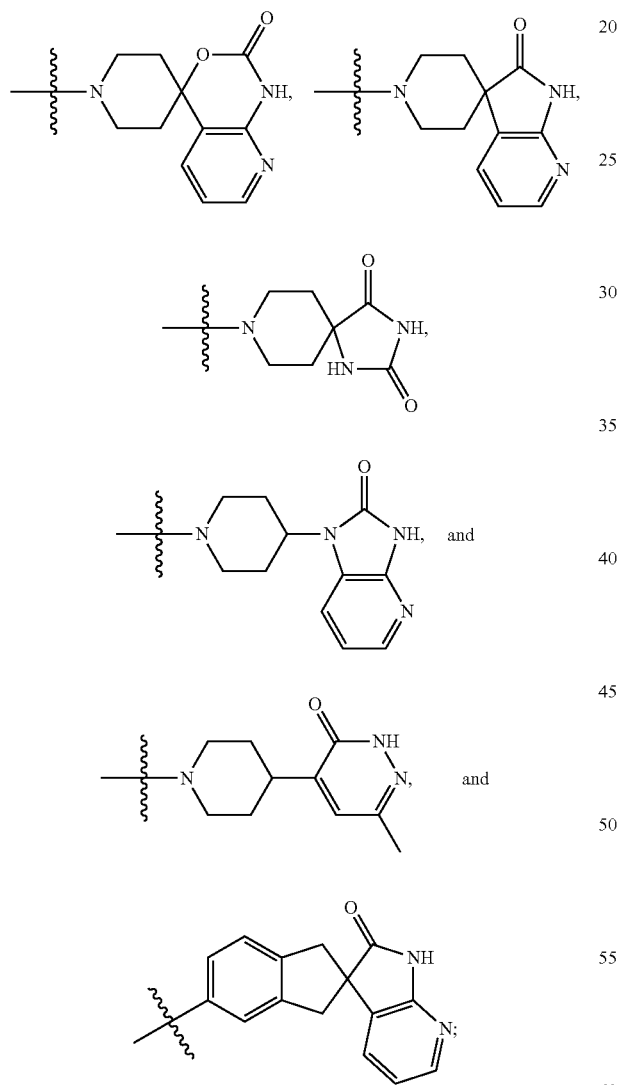

(when A is —$NR^5$).

The present invention is further directed to additional CGRP antagonists which include compounds of Formula (II), wherein:

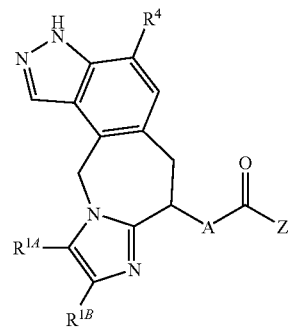

wherein $R^{1A}$, $R^{1B}$, $R^4$, A, and Z are as defined herein, and pharmaceutically acceptable salts thereof, and enantiomers and diastereomers thereof.

The present invention is further directed to additional CGRP antagonists which include compounds of Formula (III), wherein:

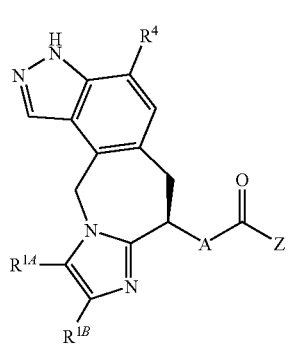

wherein $R^{1A}$, $R^{1B}$, $R^4$, A, and Z are as defined herein, and pharmaceutically acceptable salts thereof, and enantiomers and diastereomers thereof.

The present invention is further directed to the exemplary compounds 1-16 of formula (I), including:

1-(1-{[(7S)-4-chloro-10-(2,2,2-trifluoro-1,1-dimethyl-ethyl)-3,6,7,12-tetrahydroimidazo[1',2':1,7]azepino[3,4-e]indazol-7-yl]acetyl}piperidin-4-yl)-1,3-dihydro-2H-imidazo[4,5-b]pyridin-2-one (Example 1);

N-{(7R)-4-chloro-10-[1-(trifluoromethyl)cyclopropyl]-3,6,7,12-tetrahydroimidazo[1',2':1,7]azepino[3,4-e]indazol-7-yl}-4-(2-oxo-2,3-dihydro-1H-imidazo[4,5-b]pyridin-1-yl)piperidine-1-carboxamide (Example 2);

N-{(7R)-4-chloro-10-[1-(trifluoromethyl)cyclopropyl]-3,6,7,12-tetrahydroimidazo[1',2':1,7]azepino[3,4-e]indazol-7-yl}-2'-oxo-1',2'-dihydro-1H-spiro[piperidine-4,4'-pyrido[2,3-d][1,3]oxazine]-1-carboxamide (Example 3);

N-[(7R)-4-chloro-10-(1-hydroxy-1-methylethyl)-3,6,7,12-tetrahydroimidazo[1',2':1,7]azepino[3,4-e]indazol-7-yl]-2'-oxo-1,1',2',3-tetrahydrospiro[indene-2,3'-pyrrolo[2,3-b]pyridine]-5-carboxamide (Example 4);

and pharmaceutically acceptable salts thereof.

The invention is also directed to medicaments or pharmaceutical compositions for treating diseases or disorders in which CGRP is involved, such as migraine, which comprise a compound of formulas I to III, or a pharmaceutically acceptable salt thereof, and a pharmaceutically acceptable carrier.

The invention is also directed to the use of a compound of formulas I to III for treating diseases or disorders in which CGRP is involved, such as migraine.

The invention is further directed to a method for the manufacture of a medicament or a composition for treating diseases or disorders in which CGRP is involved, such as migraine, comprising combining a compound of formulas I to III with one or more pharmaceutically acceptable carriers.

It is to be understood that where one or more of the above recited structures or substructures recite multiple substituents having the same designation each such variable may be the same or different from each similarly designated variable. For example, $R^5$ is recited multiple times in formula I, and each $R^5$ in formula I may independently be any of the substructures defined under $R^5$. The invention is not limited to structures and substructures wherein each $R^5$ must be the same for a given structure. The same is true with respect to any variable appearing multiple times in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The present invention includes compounds of formula I wherein one or more hydrogen atoms are replaced by deuterium.

Tautomers of compounds defined in Formula I are also included within the scope of the present invention. For example, compounds including carbonyl —$CH_2C(O)$— groups (keto forms) may undergo tautomerism to form hydroxyl —CH═C(OH)— groups (enol forms). Both keto and enol forms are included within the scope of the present invention.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, even where substituents are disclosed which may form a ring structure (for instance $R^1$ may form a ring with another $R^1$, $R^2$ may form a ring with another $R^2$, $R^{10}$ and $R^{11}$ may form a ring, etc.), not all combinations of substituents are susceptible to ring formation. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear or branched structures having no carbon-to-carbon double or triple bonds. Thus $C_{1-6}$alkyl is defined to identify the group as having 1, 2, 3, 4, 5 or 6 carbons in a linear or branched arrangement, such that $C_{1-6}$alkyl specifically includes, but is not limited to, methyl, ethyl, n-propyl, iso-propyl, n-butyl, iso-butyl, tert-butyl, pentyl and hexyl. "Cycloalkyl" is an alkyl, part or all of which forms a ring of three or more atoms. $C_0$ or $C_0$alkyl is defined to identify the presence of a direct covalent bond, The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring.

The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The number of certain variables present in certain instances is defined in terms of the number of carbons present. For example, variable "p" is occasionally defined as follows: "p is 0 to 2q+1, for a substituent with q carbons". Where the substituent is "$(F)_p C_{1-3}$ alkyl" this means that when there is one carbon, there are up to 2(1)+1=3 fluorines. When there are two carbons, there are up to 2(2)+1=5 fluorines, and when there are three carbons there are up to 2(3)+1=7 fluorines.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacal.* 415, 39-44). Briefly, membranes (25 µg) were incubated in 1 mL of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h. The filters were washed three times with ice-cold assay buffer (10 mM HEPES, pH 7.4 and 5 mM MgCl$_2$), then the plates were air dried. Scintillation fluid (50 µL) was added and the radioactivity was counted on a Topeount (Packard Instrument). Data analysis was carried out by using Prism and the K$_i$ was determined by using the Cheng-Prusoff equation (Cheng & Prusoff (1973) *Biochem. Pharmacol.* 22, 3099-3108).

RECOMBINANT RECEPTOR: Human CL receptor (Genbank accession number L76380) was subcloned into the expression vector pIREShyg2 (BD Biosciences Clontech) as a 5'NheI and 3' PmeI fragment. Human RAMP I (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 µg/mL streptomycin, and maintained at 37° C. and 95% humidity. Cells were subcultured by treatment with 0.25% trypsin with 0.1% EDTA in HBSS. Stable cell line generation was accomplished by co-transfecting 10 µg of DNA with 30 µg Lipofectamine 2000 (Invitrogen) in 75 cm$^2$ flasks. CL receptor and RAMP I expression constructs were co-transfected in equal amounts. Twenty-four hours after transfection the cells were diluted and selective medium (growth medium+300 µg/mL hygromycin and 1 µg/mL puromycin) was added the following day. A clonal cell line was generated by single cell deposition utilizing a FACS Vantage SE (Becton Dickinson). Growth medium was adjusted to 150 µg/mL hygromycin and 0.5 µg/mL puromycin for cell propagation.

RECOMBINANT RECEPTOR BINDING ASSAY: Cells expressing recombinant human CL receptor/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 20 µg of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4 and 5 mM MgCl$_2$). Scintillation fluid was added and the plates were counted on a Topcount (Packard). Non-specific binding was determined and the data analysis was carried out with the apparent dissociation constant (K$_i$) determined by using a non-linear least squares fitting the bound CPM data to the equation below:

$$Y_{obsd} = \frac{(Y_{max} - Y_{min})(\% I_{max} - \% I_{min}/100) + Y_{min} + (Y_{max} - Y_{min})(100 - \% I_{max}/100)}{1 + ([\text{Drug}]/K_i(1 + [\text{Radiolabel}]/K_d)^{nH}}$$

Where Y is observed CPM bound, Y$_{max}$ is total bound counts, Y$_{min}$ is non specific bound counts, (Y$_{max}$−Y$_{min}$) is specific bound counts, % I$_{max}$ is the maximum percent inhibition, % 1 min is the minimum percent inhibition, radiolabel is the probe, and the K$_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; GE Healthcare). Dose response curves were plotted and IC$_{50}$ values determined from a 4-parameter logistic fit as defined by the equation y=((a−d)/(1+(x/c)$^b$)+d, where y=response, x=dose, a=max response, d=min response, c=inflection point and b=slope.

In particular, the compound of Example 4 was tested and had activity as an antagonist of the CGRP receptor in the aforementioned assays, with a K$_i$ or IC$_{50}$ value of less than 1 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an an anti-migraine agent, such as ergotamine and dihydroergotamine, or other serotonin agonists, especially a 5-$HT_{1H/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lomoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A 1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin 5$HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-$HT_1$ agonist, especially a 5-$HT_{1B/1B}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICY, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide; for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

Reaction Schemes

In one example of a synthesis of compounds of the present invention, two amines, such as 1 and 2 shown in Scheme 1, may be reacted with or 4-nitrophenylchloroformate to give the urea 3. Alternatives to or 4-nitrophenylchloroformate, for example 1,1'-carbonyldiimidazole, or phosgene, may also be effective in the formation of such ureas. The methodology illustrated in Schemes 1 and 2, as well as a wide variety of other transformations known to those skilled in the art of organic synthesis, may be used to synthesize compounds of the present invention.

SCHEME 1

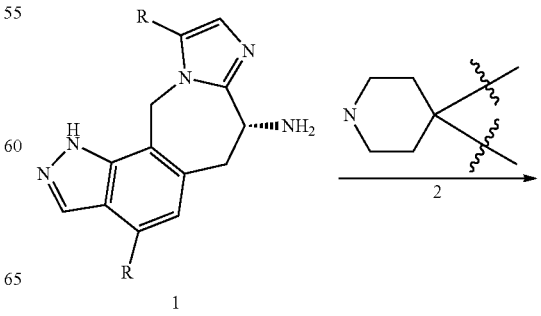

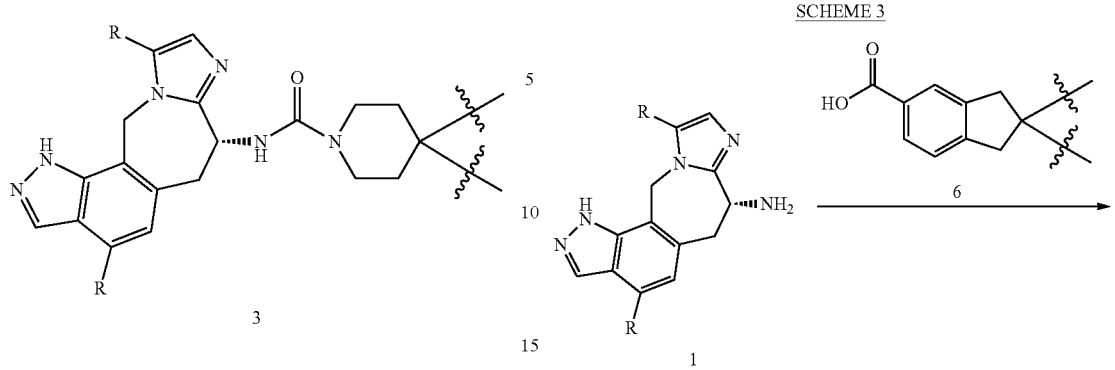

3

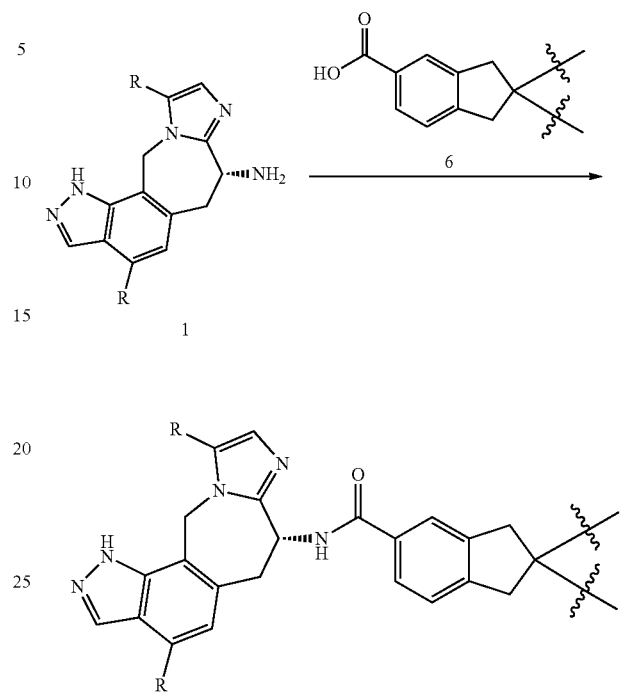

SCHEME 3

In Scheme 2, standard coupling of amines 2 with carboxylic acids (e.g. 4) may be used to provide compounds of the present invention such as structures 5. Such coupling reactions may be performed using a variety of known reagents and conditions. Examples include the use of EDC and HOBT in DMF, PyBOP in $CH_2Cl_2$, or HATU in DMF. Alternatively, the carboxylic acid may be activated, for example as the corresponding acid chloride or anhydride, to provide efficient reaction with amines of interest.

SCHEME 2

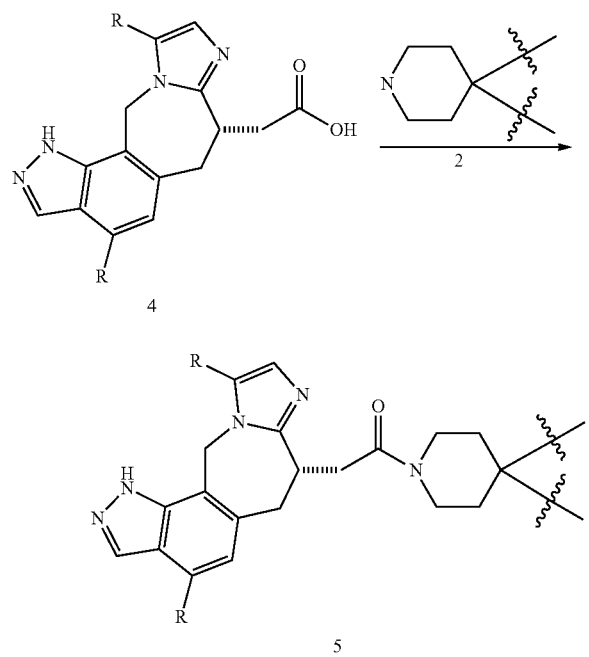

In Scheme 3, standard coupling of amines (e.g. 1) with carboxylic acids of type 6 may be used to provide compounds of the present invention such as structures 7. Such coupling reactions may be performed using a variety of known reagents and conditions. Examples include the use of EDC and HOBT in DMF, PyBOP in $CH_2Cl_2$, or HATU in DMF. Alternatively, the carboxylic acid may be activated, for example as the corresponding acid chloride or anhydride, to provide efficient reaction with amines of interest Fused imidazoles are prepared as shown in Scheme 4. Chloromethyl intermediate 8 (Chaturvedula et al. WO 2006/052378, Chaturvedula et al. WO 2006/0229447) is reacted with para methoxybenzyl amine and then cyclized with heating to caprolactam 10. The protecting groups are removed with trifluoroacetic acid and methansulfonic acid to provide amine 11 which is then protected with Boc anhydride to give 12. The thiolactam 13 is prepared by treatment with Laweson's reagent. Thioamide 13 is reacted with a variety of amino alcohols 14 in the prescence of mercury(II) chloride to give amidines 15. Oxidation of the alcohol with concommitant ring closure using either the Dess-Martin periodinane or pyridinium dichromate finally yields imidazoles of the general formula 16. Removal of the Boc protecting group with HCl gas in Ethyl acetate gives rise to the amines of general structure 1.

SCHEME 4

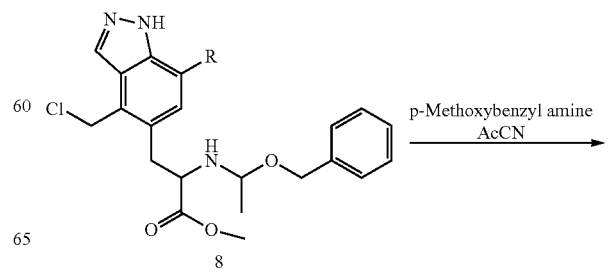

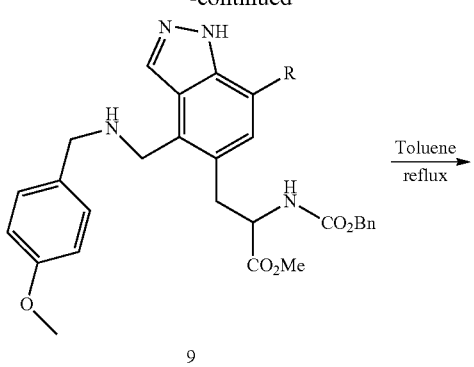
9
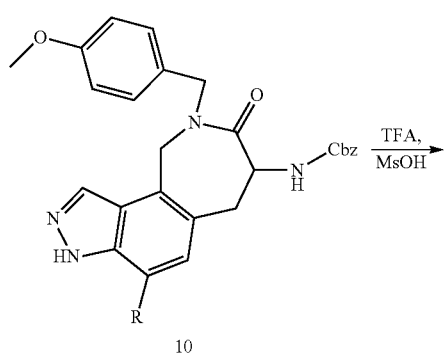
10
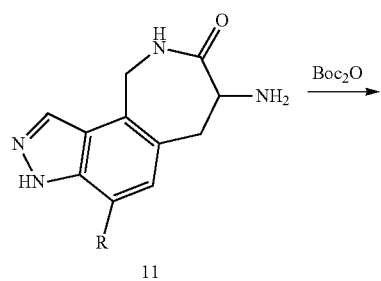
11
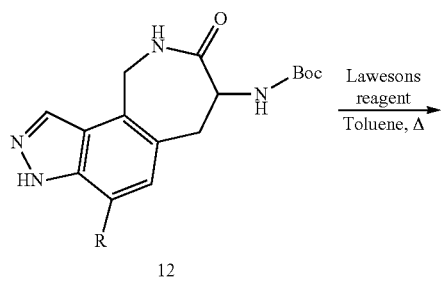
12
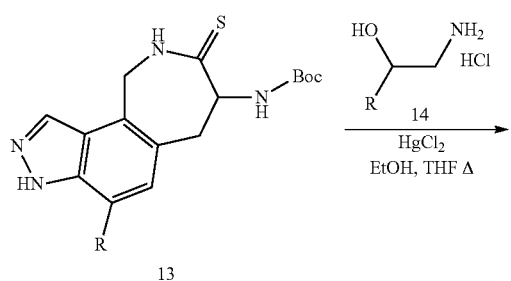
13
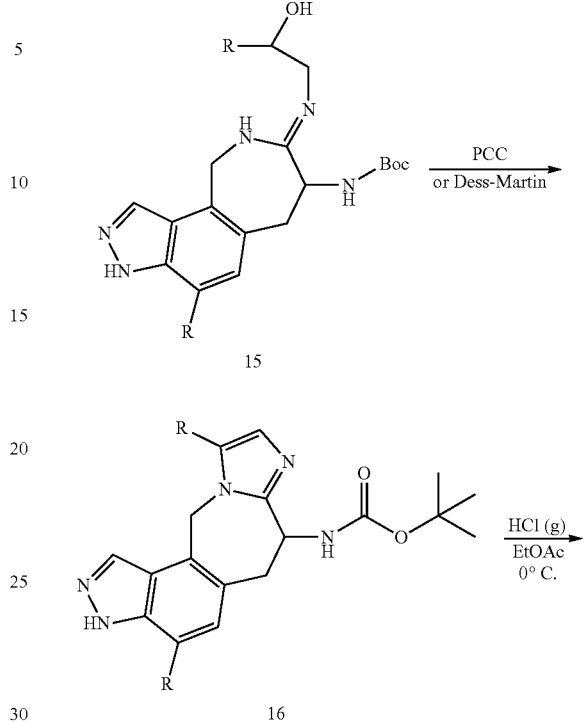
15
16
1
Alternatively intermediates 13 can be converted directly to 16 by treatment with aminoketones 17 under Mercury(II) chloride catalysis as shown in Scheme 5.
SCHEME 5
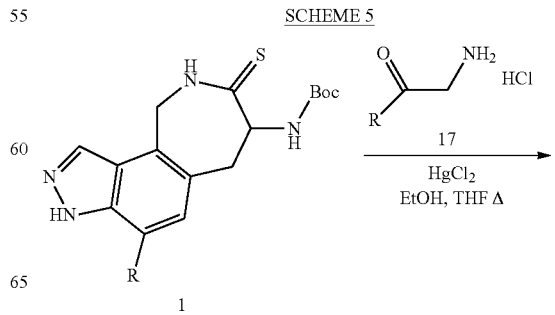
1

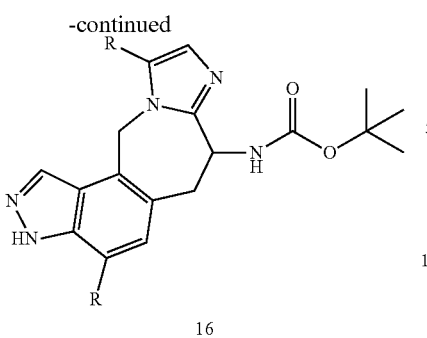

16

Fused imidazoles of general structure 4 are prepared as shown in Scheme 6. Chloromethyl intermediates 18 (Chaturvedula et al. WO 2006/052378, Chaturvedula et al. WO 2006/0229447) are reacted with paramethoxybenzyl amine and then cyclized with heating to fused caprolactam 20. The para-methoxy benzyl group is removed with Ceric ammonium nitrate and the thiolactam is prepared by treatment with Laweson's reagent. Thioamide 22 is reacted with a variety of amino alcohols 14 in the prescence of mercury(II) chloride to give amidines 23. Oxidation of the alcohol with concommitant ring closure using either the Dess-Martin periodinane or pyridinium dichromate finally yields imidazoles of the general formula 24. Alternatively thioamide 22 can be reacted directly with amino ketones such as 17 to give the fused imidazoles 24. Saponification of the ester gives compounds of general structure 4.

SCHEME 6

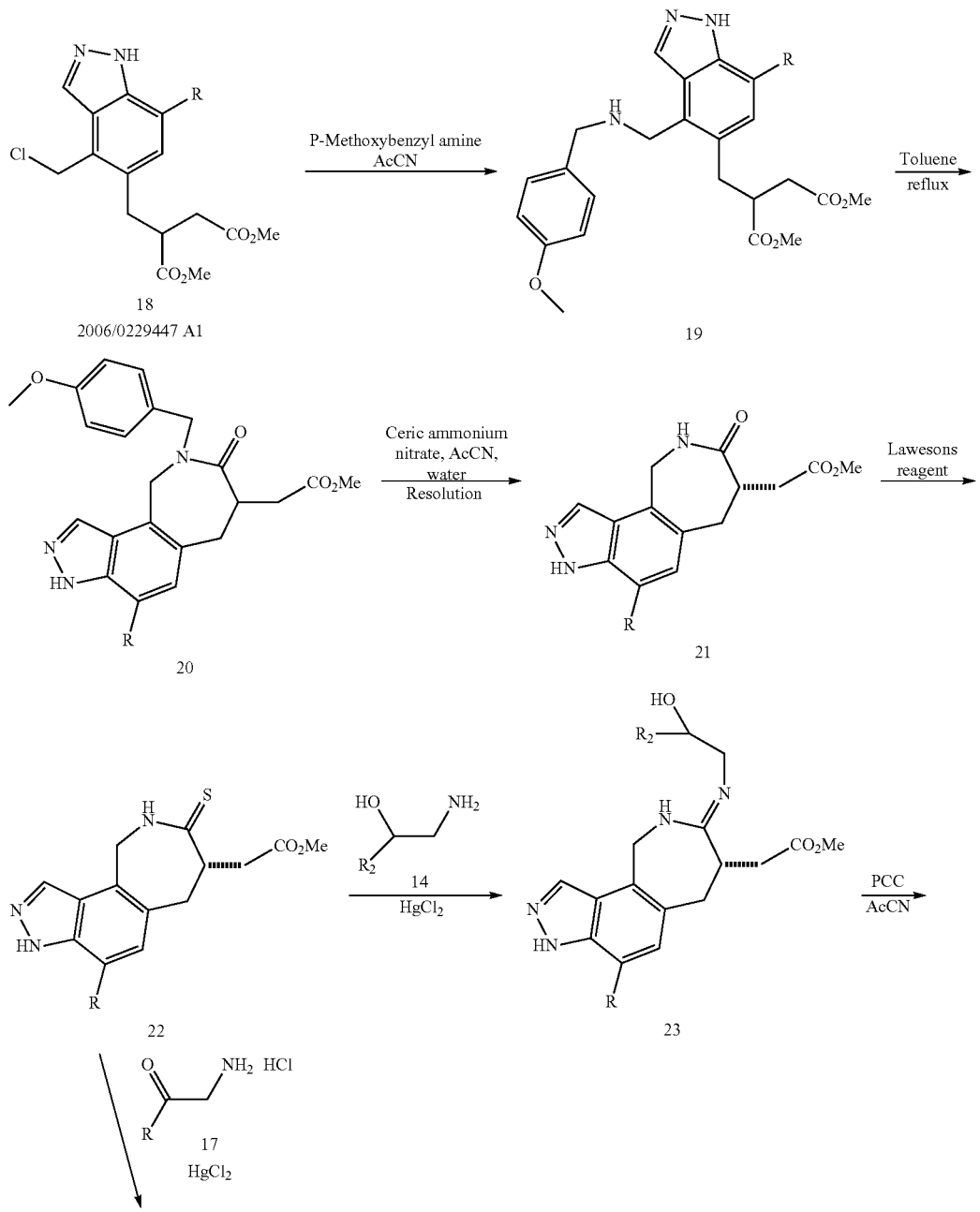

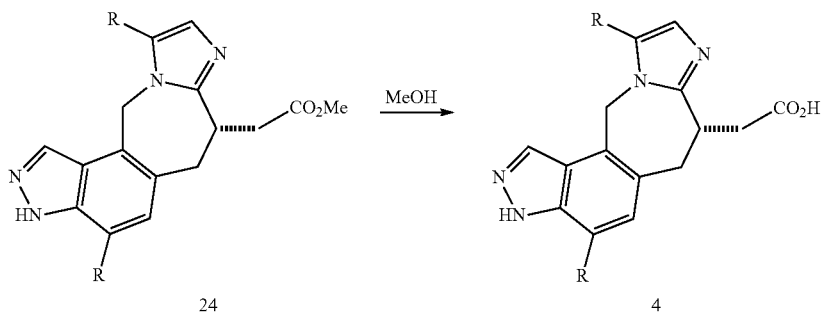

The required amino alcohols 14 for imidazole synthesis were either commercially available or prepared as shown in Scheme 7. Treatment of aldehydes 25 with trimethylsilyl cyanide gives cyanohydrins 26 which can be reduced to the appropriate amino alcohols 21 with lithium aluminum hydride.

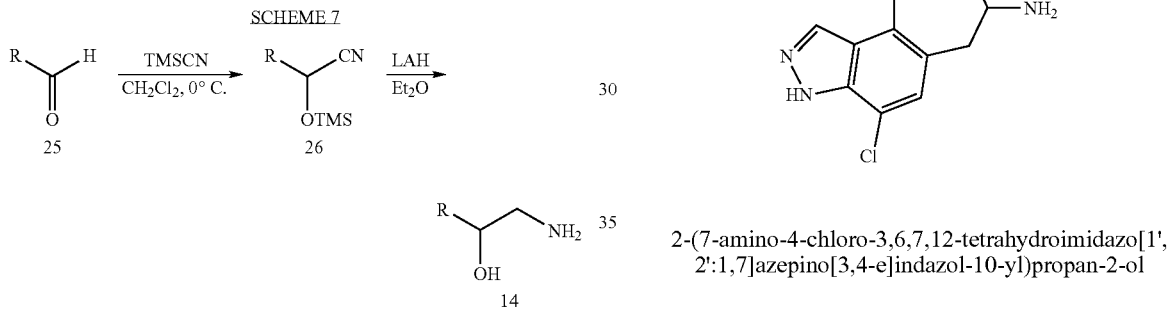

Triazole derivatives are prepared as shown in Scheme 7. Addition of hydrazine to thioamide 27 gives the corresponding hydrazide 28. Various carboxylic acids or acid chlorides can undergo couplings under standard conditions affording after ring closure the desired fused triazoles 29. Deprotection with acid provides amine 30. Conversion of 30 to compounds 31 and 32 is accomplished similar the conversions described above under conditions well known to those skilled in the art.

In some cases the final product may be further modified, for example, by manipulation of substituents. These manipulations may include, but are not limited to, reduction, oxidation, alkylation, acylation, and hydrolysis reactions which are commonly known to those skilled in the art. Moreover, in some cases the order of carrying out the foregoing reaction schemes may be varied to facilitate the reaction or to avoid unwanted reaction products.

INTERMEDIATES AND EXAMPLES

The following examples are provided so that the invention might be more fully understood. These examples are illustrative only and should not be construed as limiting the invention in any way.

Intermediate 1

2-(7-amino-4-chloro-3,6,7,12-tetrahydroimidazo[1′,2′:1,7]azepino[3,4-e]indazol-10-yl)propan-2-ol Methyl 2-{[(benzyloxy)carbonyl]amino}-3-(7-chloro-4-{[(4-methoxybenzyl)amino]methyl}-1H-indazol-5-yl)propanoate To a solution of methyl 2-{[(benzyloxy)carbonyl]amino}-3-(7-chloro-4-{chloromethyl}-1H-indazol-5-yl)propanoate (4.3 g, 9.17 mmol) in acetonitrile (100 mL) was added 4-methoxybenzyl amine (2.4 mL, 2.52 g, 18.34 mmol) and the solution stirred at room temperature for several hours. The reaction was poured into a saturated aqueous solution of sodium bicarbonate (500 mL) and the mixture extracted with ethyl acetate. The combined organic extracts were washed once with brine (100 mL), dried over anhydrous magnesium sulfate, filtered and concentrated at reduced pressure to give 4.1 g of the title compound. MS: m/z=537 (M+1).

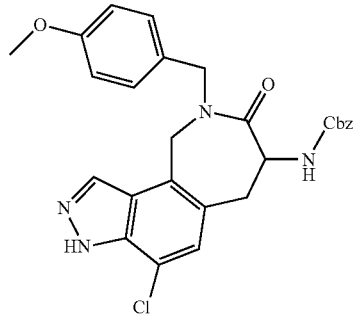 [SMILES: COc1ccc(CN2Cc3c(cc(Cl)c4[nH]ncc34)CC(NC(=O)OCc3ccccc3)C2=O)cc1]

Step B, Benzyl [4-chloro-9-(4-methoxybenzyl)-8-oxo-3,6,7,8,9,10-hexahydroazepino[3,4-e]indazol-7-yl]carbamate A solution of Methyl 2-{[(benzyloxy)carbonyl]amino}-3-(7-chloro-4-{[(4-methoxybenzyl)amino]methyl}-1H-indazol-5-yl)propanoate from Step A in toluene (100 mL) was heated at reflux for 3 hours and then cooled to room temperature. The reaction mix was poured into a saturated aqueous solution of sodium bicarbonate and the mixture was extracted with Ethyl acetate (2×200 mL). The combined organic extracts were washed once with brine (100 mL), dried over anhydrous sodium sulfate, filtered and concentrated at reduced pressure. The resulting solid was swished once with a 1:1 mix of ethylacetate/hexane and the solid collected by filtration to give 3.1 g of the title compound to give the title compound. MS: m/z 505 (M+1).

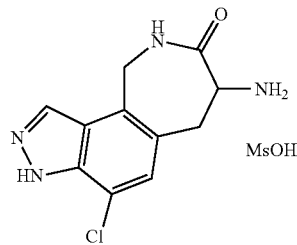

Step C. 7-amino-4-chloro-6,7,9,10-tetrahydroazepino[3,4-e]indazol-8(3H)-one methanesulfonate To a solution of Benzyl [4-chloro-9-(4-methoxybenzyl)-8-oxo-3,6,7,8,9,10-hexahydroazepino[3,4-e]indazol-7-yl]carbamate from Step B in trifluoroacetic acid (15 mL) was added methanesulfonic (3 mL) acid at room temperature and the reaction allowed to stir at room temperature for several hours until LC analysis indicated reaction completion. The reaction was carefully poured into 1 L of ethyl ether and the resulting solid collected by filtration to give 3 g of the title compound. MS: m/z=251 (M+1).

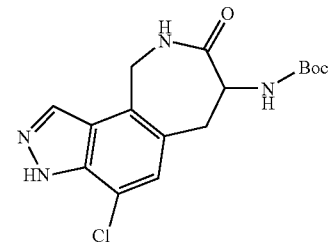 [SMILES: CC(C)(C)OC(=O)NC1Cc2cc(Cl)c3[nH]ncc3c2CNC1=O]

Step D. Tert-Butyl (4-chloro-8-oxo-3,6,7,8,9,10-hexahydroazepino[3,4-e]indazol-7-yl)carbamate To a solution of 7-amino-4-chloro-6,7,9,10-tetrahydroazepino[3,4-e]indazol-8(3H)-one methanesulfonate from Step C in 1:1 THF/water (100 mL) was added diisopropyl ethylamine (1.1 g, 1.58 mL, 8.65 mmol) and Boc-anhydride (1.88 g, 8.65 mmol) and the reaction allowed to stir at room temperature for 30 minutes. The reaction was poured into a solution of saturated aqueous sodium bicarbonate and the mixture was extracted with ethyl acetate (3×100 mL). The combined organic extracts were washed once with brine (100 mL), dried over anhydrous magnesium sulfate, filtered and concentrated at reduced pressure to give 900 mg of the title compound. MS: m/z=351 (M+1).

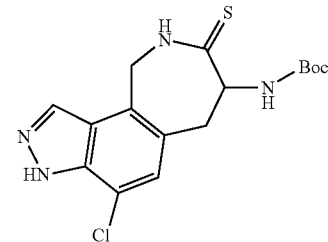 [SMILES: CC(C)(C)OC(=O)NC1Cc2cc(Cl)c3[nH]ncc3c2CNC1=S]

Step E. Tert-Butyl (4-chloro-8-thioxo-3,6,7,8,9,10-hexahydroazepino[3,4-e]indazol-7-yl)carbamate A mixture of tert-butyl (4-chloro-8-oxo-3,6,7,8,9,10-hexahydroazepino[3,4-e]indazol-7-yl)carbamate from Step D (800 mg, 2.28 mmol) and Laweson's reagent (922 mg, 2.28 mmol) in toluene (100 mL) was heated to reflux for 1 hour and then cooled to room temperature and allowed to stand overnight. The solid was collected by filtration to give 800 mg of the title compound. MS: m/z=366 (M+1).

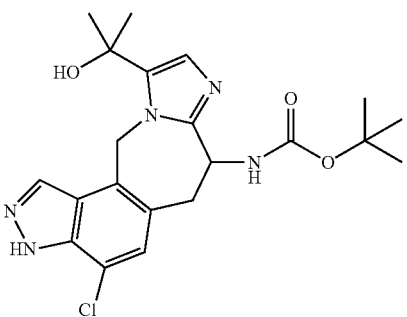 [SMILES: CC(C)(C)OC(=O)NC1Cc2cc(Cl)c3[nH]ncc3c2Cn2c(C(C)(C)O)cnc21]

Step F. Tert-Butyl [4-chloro-10-(1-hydroxy-1-methylethyl)-3,6,7,12-tetrahydroimidazo[1',2':1,7]azeino 3,4-e]indazol-7-carbamate To a solution of tert-butyl (4-chloro-8-thioxo-3,6,7,8,9,10-hexahydroazepino[3,4-d]ndazol-7-yl)carbamate (200 mg, 0.55 mmol) and 1-amino-3-hydroxy-3-methylbutan-2-one Tosylate (170 mg, 0.58 mmol) in Ethanol (5 mL) and THF (15 mL) was added mercury (II) chloride and diisopropylethyl amine (282 mg, 380 uL, 2.18 mmol) and the reaction heated to 60° C. overnight. The reaction mixture was cooled to room temperature and filtered thru a pad of diatomaceous earth and the filtrate concentrated. The material was chromatographed on silica gel eluting with a gradient of 2% Methanol/Dichloromethane to 10% Methanol/Dichloromethane. The pure fractions were combined and concentrated at reduced pressure to give 180 mg of the title compound. MS: m/z=432 (M+1).

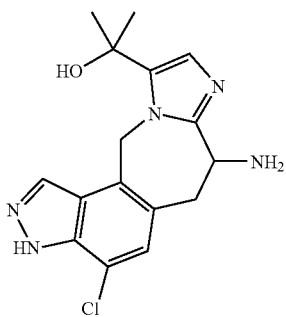 [SMILES: CC(C)(O)c1cnc2n1Cc1c(cc(Cl)c3[nH]ncc13)CC2N]

Step G. 2-(7-Amino-4-chloro-3,6,7,12-tetrahydroimidazo[1',2':1,7]azepino[3,4-e]indazol-10-yl)propan-2-ol hydrochloride A solution of tert-butyl [4-chloro-10-(1-hydroxy-1-methylethyl)-3,6,7,12-tetrahydroimidazo[1',2':1,7]azepino[3,4-e]indazol-7-yl]carbamate from Step F in Ethyl acetate (50 mL) was cooled to 0° C. HCl gas was bubbled into the solution until saturated and the reaction allowed to warm slowly to room temperature. The reaction was concentrated at reduced pressure and dried to give a quantitative yield of the title compound. MS: m/z 331 (M+1).

Example 1

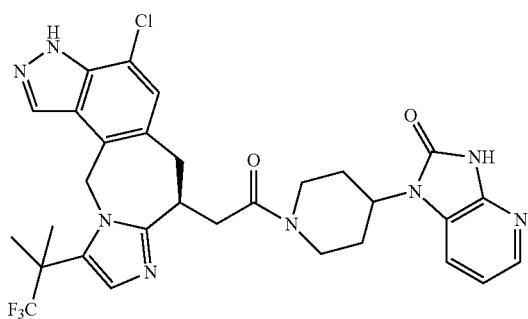 [SMILES: CC(C)(c1cnc2n1Cc1c(cc(Cl)c3[nH]ncc13)C[C@H]2CC(=O)N1CCC(n2c(=O)[nH]c3ncccc32)CC1)C(F)(F)F]

1-(1-{[(7S)-4-chloro-10-(2,2,2-trifluoro-1,1-dimethylethyl)-3,6,7,12-tetrahydroimidazo[1',2':1,7]azepino [3,4-e]indazol-7-yl]acetyl}piperidin-4-yl)-1,3-dihydro-2H-imidazo[4,5-b]pyridin-2-one A mixture of [(7S)-4-chloro-10-(2,2,2-trifluoro-1,1-dimethylethyl)-3,6,7,12-tetrahydroimidazo[1',2':1,7]azepino[3,4-e]indazol-7-yl]acetic acid (100 mg, 0.275 mmol), 1-Piperidin-4-yl-1,3-dihydro-2H-imidazo[4,5-b]pyridin-2-one dihydrochloride [Bergey et al. WO 2006/044504], HOBT (43 mg, 0.28 mmol), EDC (54 mg, 0.28 mmol) and N,N-diisopropylethylamine (48 uL, 0.28 mmol) in DMF (2 mL) is stirred at ambient temperature for 18 h. The reaction mixture is purified directly by HPLC using a reversed phase C18 column and eluting with a gradient of H$_2$O:CH$_3$CN:CF$_3$CO$_2$H-90:10:0.1 to 5:95:0.1. The pure, product-containing fractions are combined and made basic with saturated aqueous NaHCO$_3$. The resulting mixture is extracted with EtOAc (2×20 mL), and the combined organic extracts are washed with brine, dried over Na$_2$SO$_4$, filtered, and concentrated in vacuo to provide the title compound.

Example 2

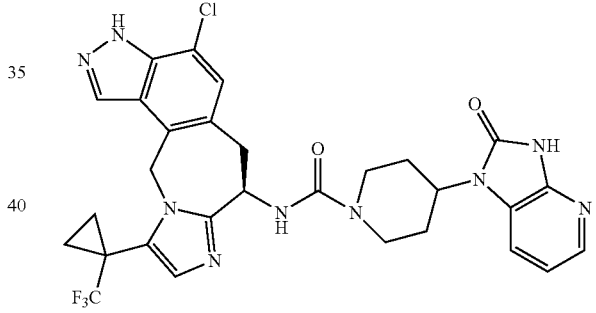

N-{(7R)-4-chloro-10-[1-(trifluoromethyl)cyclopropyl]-3,6,7,12-tetrahydroimidazo[1',2':1,7]azepino[3,4-e]indazol-7-yl}-4-(2-oxo-2,3-dihydro-1H-imidazo[4,5-b]pyridin-1-yl)piperidine-1-carboxamide To solution of (7R)-4-chloro-10-[1-(trifluoromethyl)cyclopropyl]-3,6,7,12-tetrahydroimidazo[1',2':1,7]azepino[3,4-e]indazol-7-amine (100 mg, 0.3 mmol) and triethyl amine (120 uL, 0.9 mmole) is added 4-nitrophenyl chloroformate (60 mg, 0.3 mmol) and stirred at 0° C. for 1 hr. 1-Piperidin-4-yl-1,3-dihydro-2H-imidazo[4,5-b]pyridin-2-one dihydrochloride [Burgey et al. WO 2006/044504], (87 mg, 0.3 mmol), is added along with triethylamine (120 uL, 0.9 mmol) and the reaction mixture is stirred at ambient temperature for 18 h. Saturated aqueous sodium carbonate (50 mL) is added and the mixture is extracted with dichloromethane (3×25 mL) The combined organic layers are washed with saturated aqueous sodium bicarbonate, brine, dried over sodium sulfate, filtered and concentrated. Purification by silica gel chromatography [100% dichloromethane→93% dichloromethane/methanol] provides the title compound.

Example 3

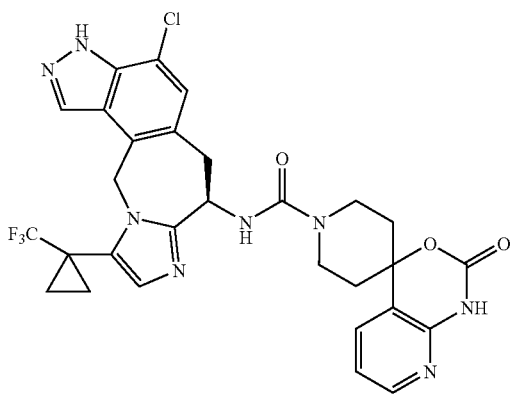 [SMILES: O=C1Nc2ncccc2C2(CCN(C(=O)N[C@@H]3Cc4cc(Cl)c5[nH]ncc5c4Cn4c(C5(C(F)(F)F)CC5)cnc43)CC2)O1]

N-{(7R)-4-chloro-10-[1-(trifluoromethyl)cyclopropyl]-3,6,7,12-tetrahydroimidazo[1',2':1,7]azepino[3,4-e]indazol-7-yl}-2'-oxo-1',2'-dihydro-1H-spiro[piperidine-4,4'-pyrido[2,3-d][1,3]oxazine]-1-carboxamide To a solution of (7R)-4-chloro-10-[1-(trifluoromethyl)cyclopropyl]-3,6,7,12-tetrahydroimidazo[1',2':1,7]azepino[3,4-e]indazol-7-amine (100 mg, 0.3 mmol)], and triethylamine (120 uL, 0.9 mmole) is added p-nitrophenyl chloroformate (60 mg, 0.3 mmol) and stirred at 0° C. for 1 hr. Spiro[piperidine-4,4'-pyrido[2,3-d][1,3]oxazin]-2'(1'H)-one hydrochloride [Burgey et al. WO 2006/044504], (77 mg, 0.3 mmole is then added with triethylamine (120 uL, 0.675 mmol) and the reaction mixture is stirred at ambient temperature for 16 hrs. Saturated aqueous sodium carbonate (50 mL) is added and the mixture is extracted with dichloromethane (3×25 mL). The organic layer is washed with saturated aqueous sodium bicarbonate (3×), brine, dried over sodium sulfate, filtered and concentrated. Purification by silica gel chromatography [100% dichloromethane→93% dichloromethane/methanol] gives the title compound.

Example 4

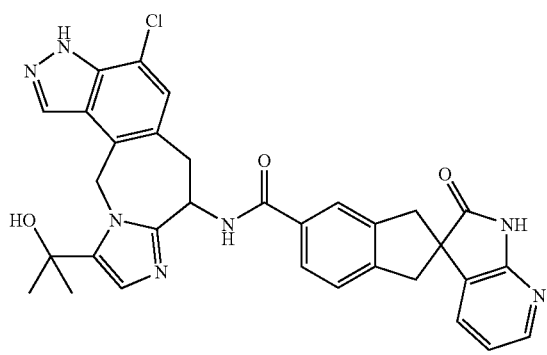 [SMILES: CC(C)(O)c1cnc2n1Cc1c(cc(Cl)c3[nH]ncc13)CC2NC(=O)c1ccc2c(c1)CC1(C2)C(=O)Nc2ncccc21]

N-[(7R)-4-chloro-10-(1-hydroxy-1-methylethyl)-3,6,7,12-tetrahydroimidazo[1',2':1,7]azepino[3,4-e]indazol-7-yl]-2'-oxo-1,1',2',3-tetrahydrospiro[indene-2,3'-pyrrolo[2,3-b]pyridine]-5-carboxamide A solution of 2-[7-amino-4-chloro-3,6,7,12-tetrahydroimidazo[1',2':1,7]azepino[3,4-e]indazol-10-yl]propan-2-ol (100 mg, 0.3 mmole) and (±)-2'-oxo-1,1',2',3-tetrahydrospiro[indene-2,3'-pyrrolo[2,3-b]pyridine]-5-carboxylic acid (78 mg, 0.28 mmol) [Bell et al. WO 2006/031606], HOBT (43 mg, 0.28 mmol), and EDC (54 mg, 0.28 mmol) in DMF (2 mL) was stirred at ambient temperature for 1 h. The reaction mixture was purified directly by HPLC using a reversed phase C18 column and eluting with a gradient of $H_2O:CH_3CN:CF_3CO_2H$-90:10:0.1 to 5:95:0.1. The pure, product-containing fractions were combined and made basic with saturated aqueous $NaHCO_3$. The resulting mixture was extracted with EtOAc (2×20 mL), and the combined organic extracts were washed with brine, dried over $Na_2SO_4$, filtered, and concentrated in vacuo to provide the title compound as an off white solid. MS: m/z=594 (M+1)

Examples 5-20

Following procedures substantially as described above and using intermediates described in a number of publications including, but not limited to, Burgey et al. WO 2004/092168, and Burgey et al. WO 2006/044504, the following compounds may be prepared:

Example 5

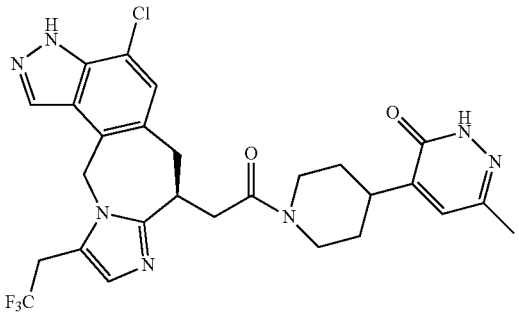

Example 6

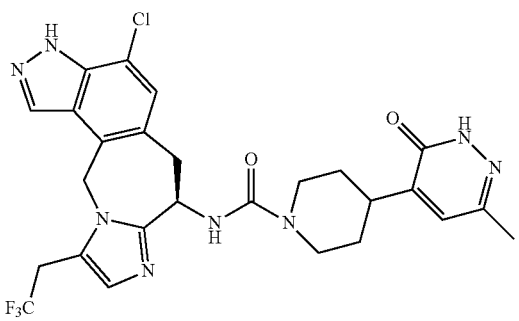

Example 7
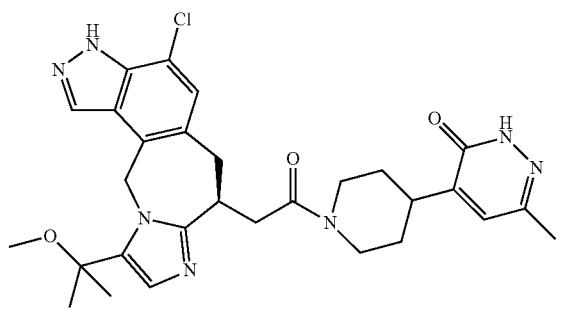
Example 8
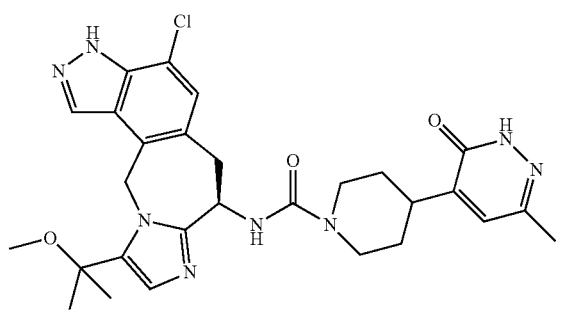
Example 9
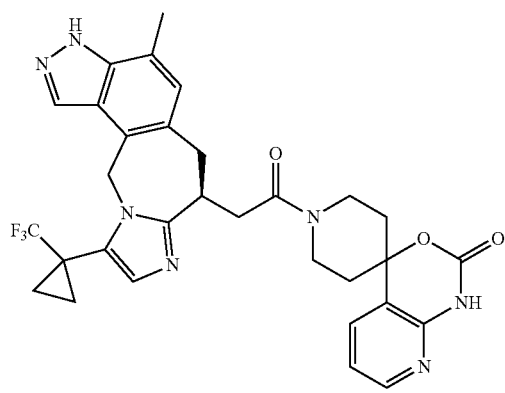
Example 10
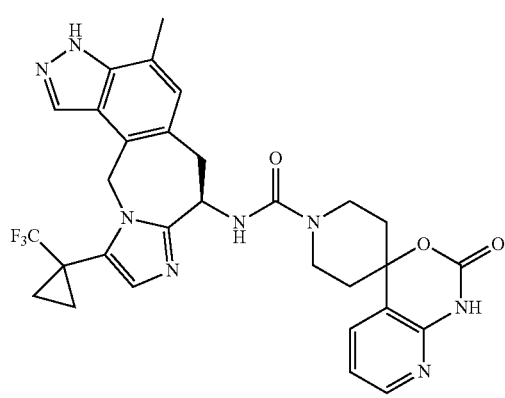
Example 11
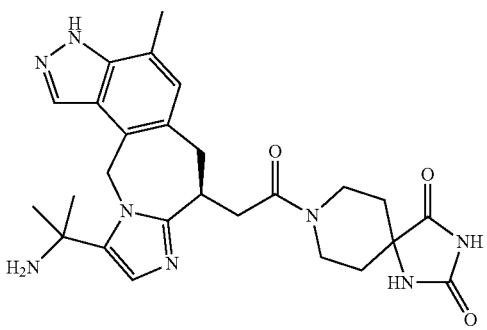
Example 12
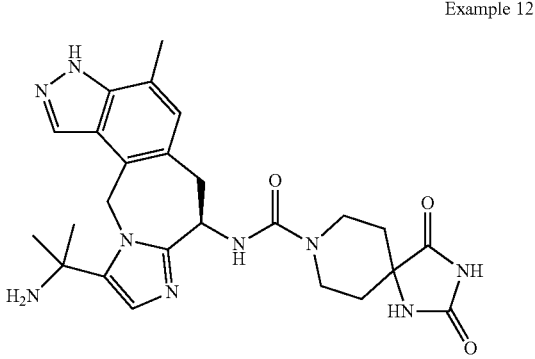
Example 13
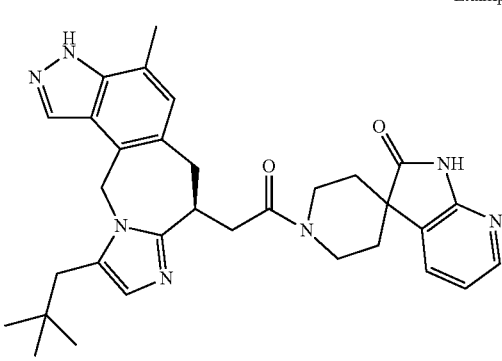
Example 14
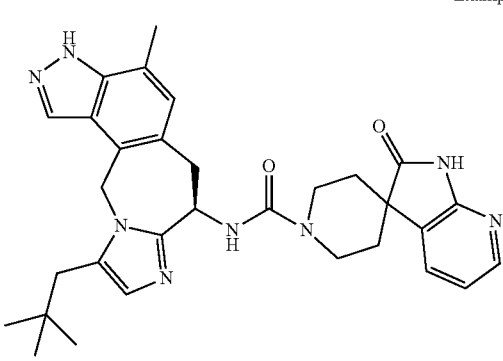

-continued

Example 15

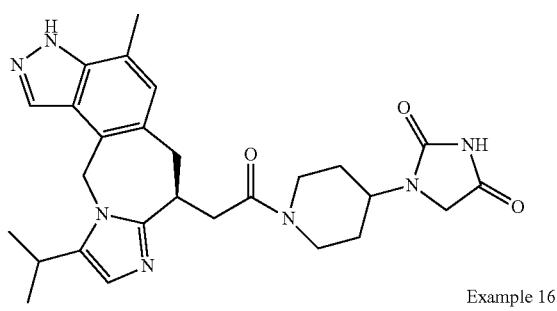

Example 16

Example 17

Example 18

Example 19

-continued

Example 20

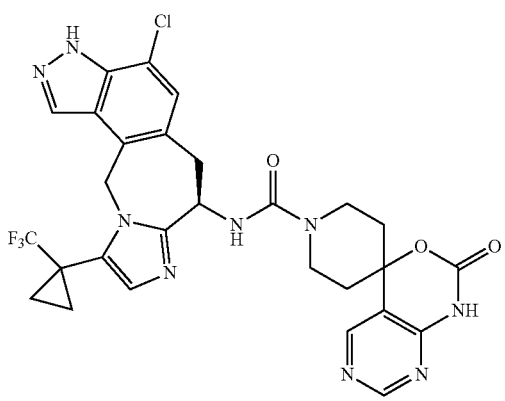

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of formula (II):

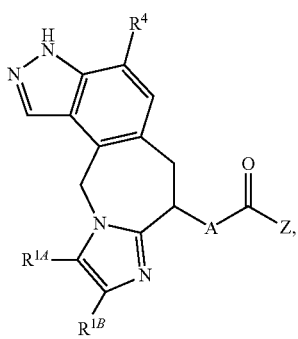

(II)

wherein:

A is $NR^5$ or $C(R^5)_2$;

Z is selected from:
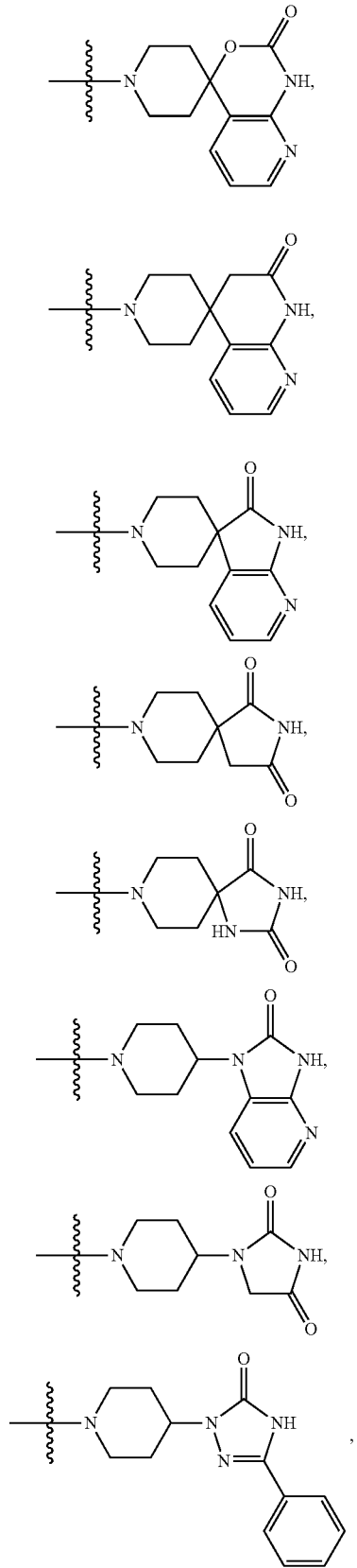
-continued
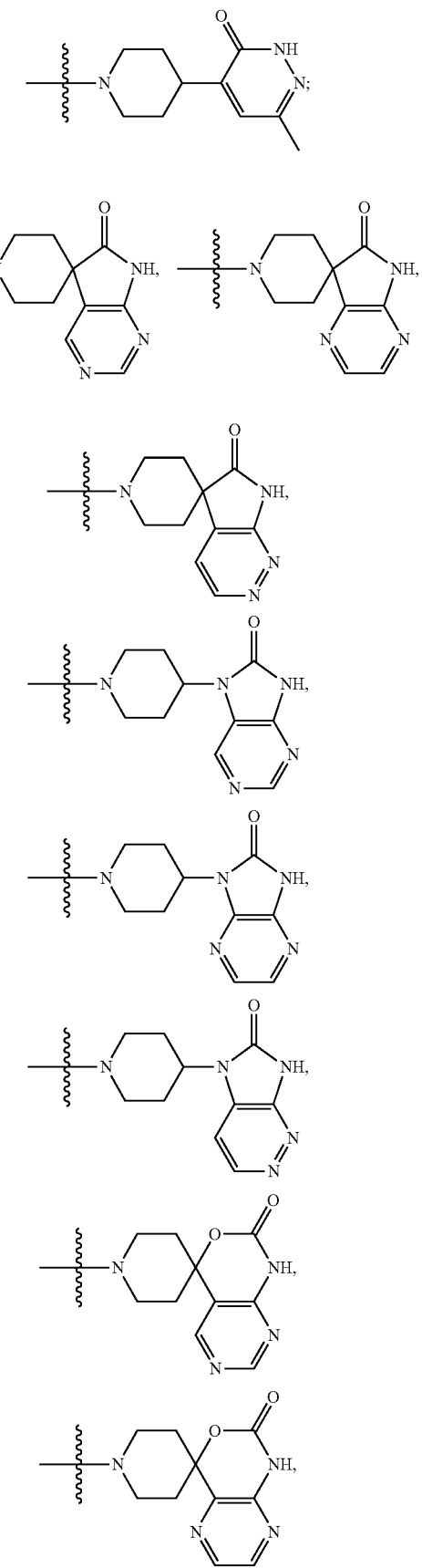

-continued

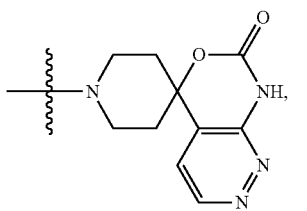

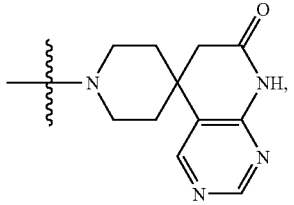

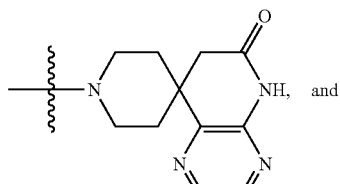 and

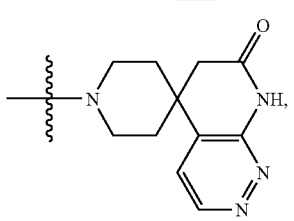

and when A is NR⁵, Z is additionally selected from:

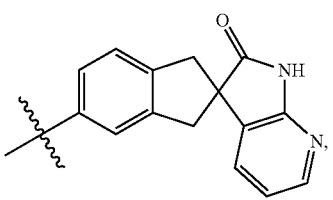

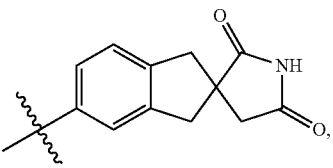

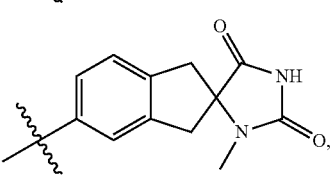

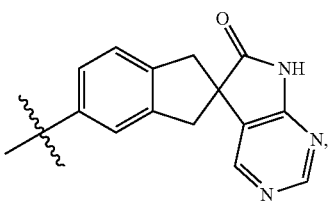

-continued

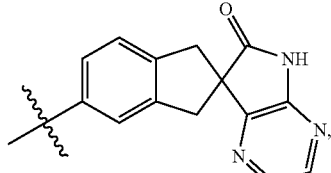

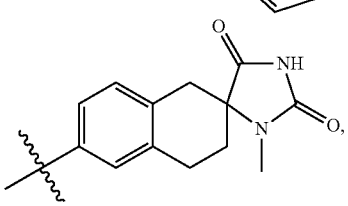

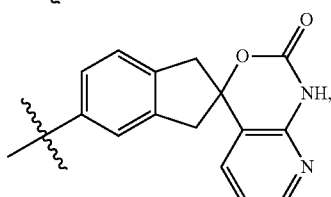

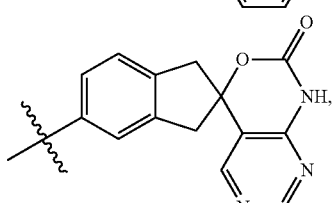

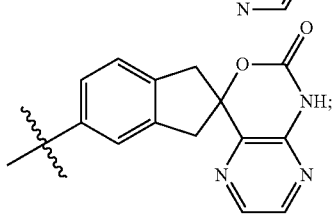

$R^{1A}$ and $R^{1B}$ are independently selected from:
1) H, $C_1$-$C_6$ alkyl, $C_{3-6}$ cycloalkyl and heterocycle, wherein said alkyl, cycloalkyl and heterocycle is optionally substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^5$,
   d) heteroaryl, unsubstituted or substituted with 1-5 substituents each independently selected from $R^5$,
   e) heterocycle, unsubstituted or substituted with 1-5 substituents each independently selected from $R^5$,
   f) $(F)_p C_{1-3}$ alkyl,
   g) halogen,
   h) $OR^5$,
   i) $O(CH_2)_s OR^5$,
   j) $CO_2 R^5$,
   k) CN,
   l) $NR^{10} R^{11}$, and
   m) $O(CO) R^5$; and
2) aryl or heteroaryl, wherein said aryl or heteroaryl is optionally substituted with one or more substituents independently selected from:
   a) $C_{1-6}$ alkyl,
   b) $C_{3-6}$ cycloalkyl, c) $(F)_pC_{1-3}$ alkyl,
d) halogen,
e) $OR^5$,
f) $CO_2R^5$,
g) $(CO)NR^{10}R^{11}$,
h) $SO_2NR^{10}R^{11}$,
i) $N(R^{10})SO_2R^{11}$,
j) $S(O)_mR^5$,
k) CN,
l) $NR^{10}R^{11}$, and
m) $O(CO)R^4$;

$R^4$ is hydrogen, halo, $C_{1-6}$ alkyl, or $C_{2-6}$ alkenyl;

$R^5$ is selected from: H, $C_{1-6}$ alkyl, $C_{3-6}$ cycloalkyl, aryl, heteroaryl and benzyl, wherein said alkyl, cycloalkyl, aryl or heteroaryl moiety is optionally substituted with halogen, hydroxy or $C_1$-$C_6$ alkoxy;

$R^{10}$ and $R^{11}$ are independently selected from: H, $C_{1-6}$ alkyl, $C_{3-6}$ cycloalkyl, aryl, heteroaryl and benzyl, wherein said alkyl, cycloalkyl, aryl or heteroaryl moiety is optionally substituted with halogen, hydroxy or $C_1$-$C_6$ alkoxy, provided that when $R^{10}$ and $R^{11}$ are bonded to the same nitrogen atom, then $R^{10}$ and $R^{11}$ and the nitrogen to which they are both attached form a ring selected from: azetidinyl, pyrrolidinyl, piperidinyl, piperazinyl and morpholinyl, which ring is unsubstituted or substituted with 1-5 substituents each independently selected from $R^5$;

p is 0 to 2q+1, for a substituent with q carbons
m is 0 to 2;
s is 1 to 3
or a pharmaceutically acceptable salt thereof, or individual stereoisomer thereof.

2. A compound of claim 1, or a pharmaceutically acceptable salt or individual stereoisomer thereof, wherein $R^{1B}$ is hydrogen, and $R^{14}$ is:

1) H, $C_{1-6}$ alkyl, $C_{3-6}$ cycloalkyl or heterocycle, wherein said alkyl, cycloalkyl or heterocycle is optionally substituted with one or more substituents which are independently:
  a) $C_{1-6}$ alkyl,
  b) $C_{3-6}$ cycloalkyl,
  c) phenyl, unsubstituted or substituted with 1-5 substituents each independently selected from $R^5$,
  d) heteroaryl, unsubstituted or substituted with 1-5 substituents each independently selected from $R^5$, and where heteroaryl is selected from:
    imidazole, isoxazole, oxazole, pyrazine, pyrazole, pyridazine, pyridine, pyrimidine, and thiazole;
  e) heterocycle, unsubstituted or substituted with 1-5 substituents each independently selected from $R^5$, and where heterocycle is selected from:
    azetidine, dioxane, dioxolane, morpholine, oxetane, piperazine, piperidine, pyrrolidine, tetrahydrofuran, and tetrahydropyran;
  f) $(F)_pC_{1-3}$ alkyl,
  g) halogen,
  h) $OR^5$,
  i) $O(CH_2)_sOR^5$,
  j) $CO_2R^5$,
  k) CN,
  l) $NR^{10}R^{11}$, or
  m) $O(CO)R^5$; or 2) aryl or heteroaryl, selected from: phenyl, imidazole, isoxazole, oxazole, pyrazine, pyrazole, pyridazine, pyridine, pyrimidine, and thiazole, wherein said aryl or heteroaryl is optionally substituted with one or more substituents which are independently:
  a) $C_{1-6}$ alkyl,
  b) $C_{3-6}$ cycloalkyl,
  c) $(F)_pC_{1-3}$ alkyl,
  d) halogen,
  e) $OR^5$,
  f) $CO_2R^5$,
  g) $(CO)NR^{10}R^{11}$,
  h) $SO_2NR^{10}R^{11}$,
  i) $N(R^{10})SO_2R^{11}$,
  j) $S(O)_mR^5$,
  k) CN,
  l) $NR^{10}R^{11}$, or
  m) $O(CO)R^4$.

3. A compound of claim 2, or a pharmaceutically acceptable salt or individual stereoisomer thereof, wherein $R^{14}$ is $C_{1-6}$ alkyl or $C_{3-6}$ cycloalkyl, optionally substituted with one or more substituents each independently selected from:
  a) $C_{1-6}$ alkyl,
  b) halogen,
  c) OH,
  d) O $C_{1-6}$ alkyl, and
  e) $NR^{10}R^{11}$.

4. A compound of claim 1, or a pharmaceutically acceptable salt or individual stereoisomer thereof, wherein $R^4$ is hydrogen, $C_{1-6}$ alkyl, or halo.

5. A compound of claim 1, or a pharmaceutically acceptable salt or individual stereoisomer thereof, wherein A is —$CH_2$—.

6. A compound of claim 1, or a pharmaceutically acceptable salt or individual stereoisomer thereof, wherein A is —NH—.

7. A compound of claim 1, or a pharmaceutically acceptable salt or individual stereoisomer thereof, wherein Z is:

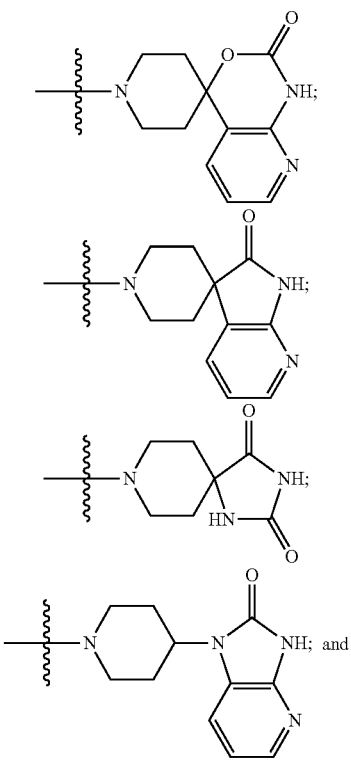

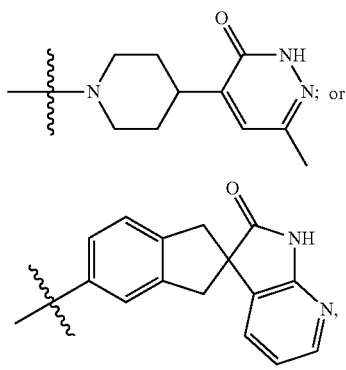
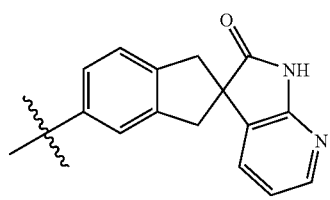 [SMILES: *c1ccc2c(c1)CC1(C2)C(=O)Nc2ncccc21] or
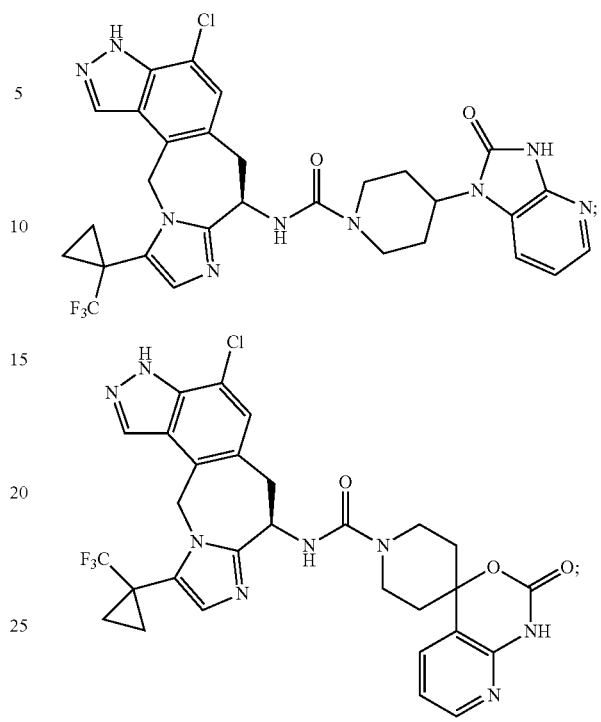
provided that Z is selected to be
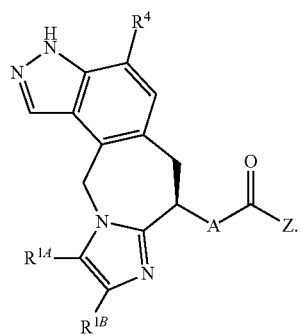
only when A is selected to be NR⁵.
8. A compound of claim 1, or a pharmaceutically acceptable salt thereof, or individual stereoisomer thereof, wherein, the structure of Formula II has the structure of Formula (III):
(III)
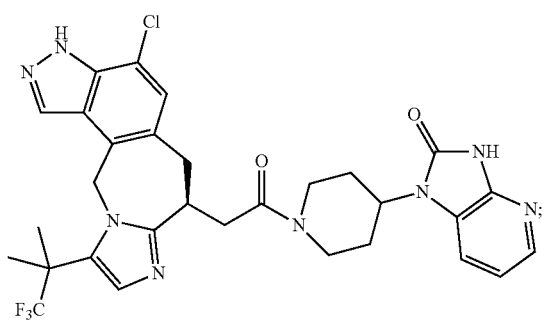
9. A compound of claim 1, or a pharmaceutically acceptable salt thereof, or individual stereoisomer thereof, which is:
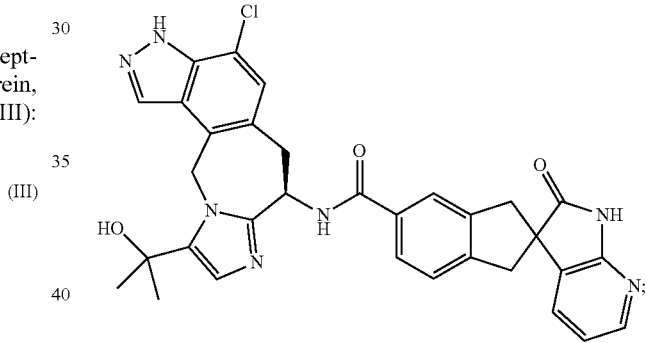
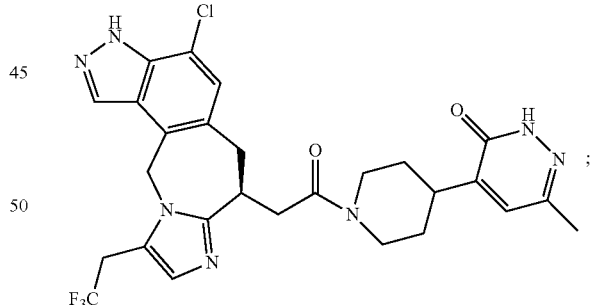
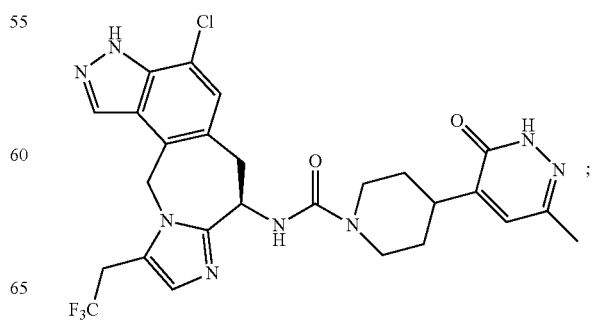

49
-continued
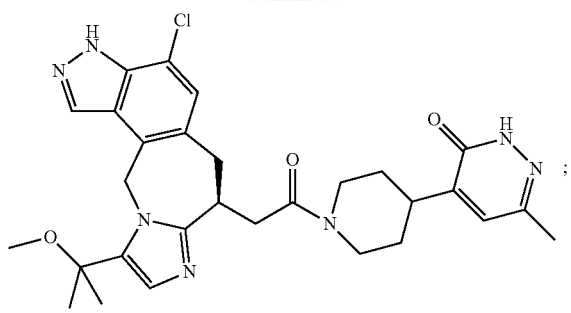
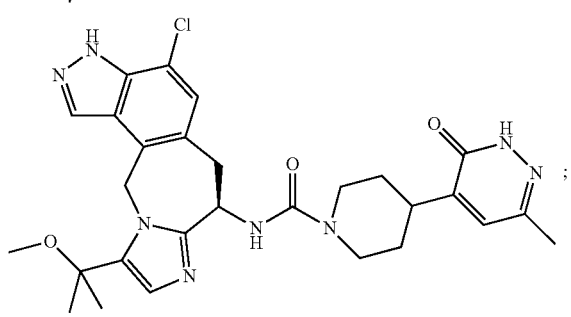
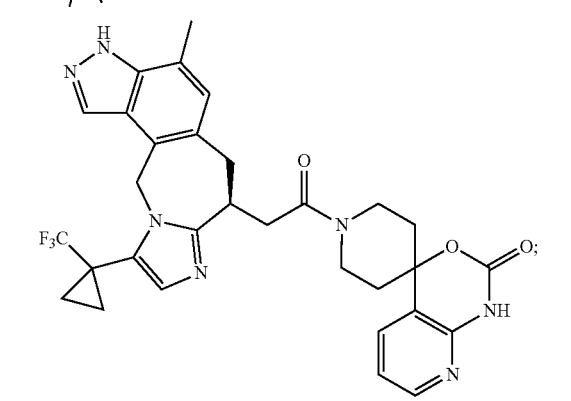
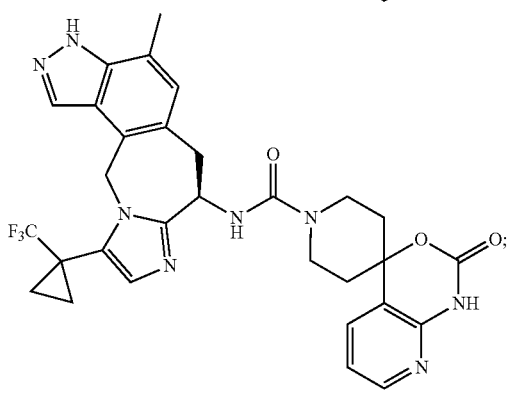
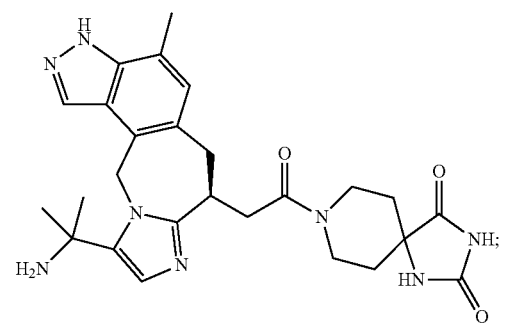
50
-continued
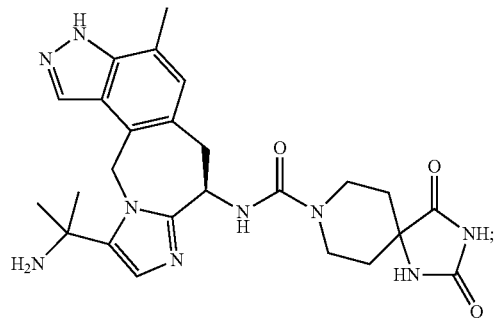
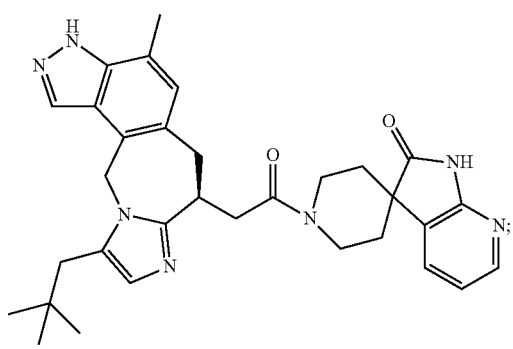
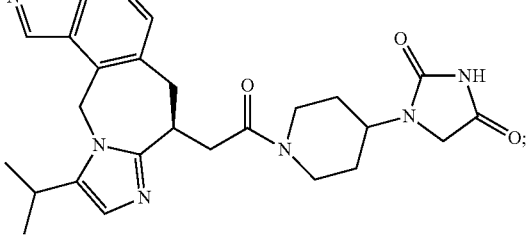

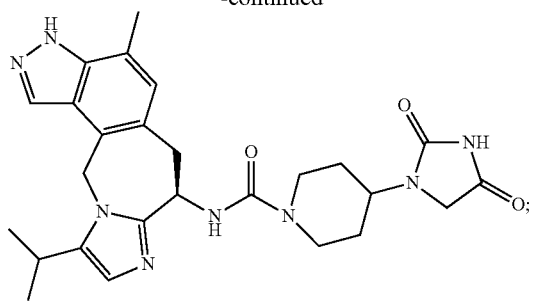

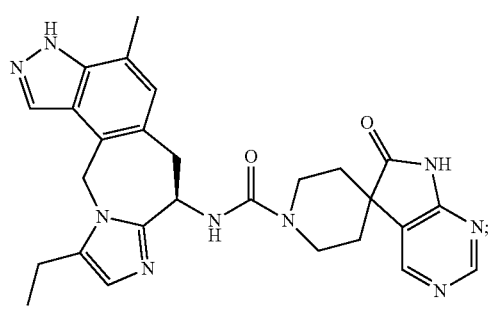

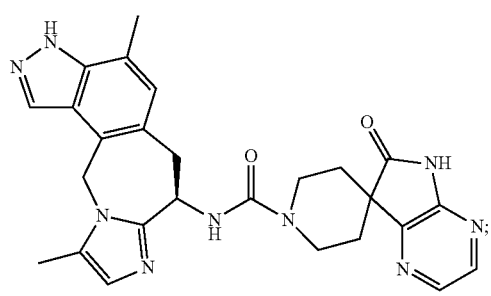

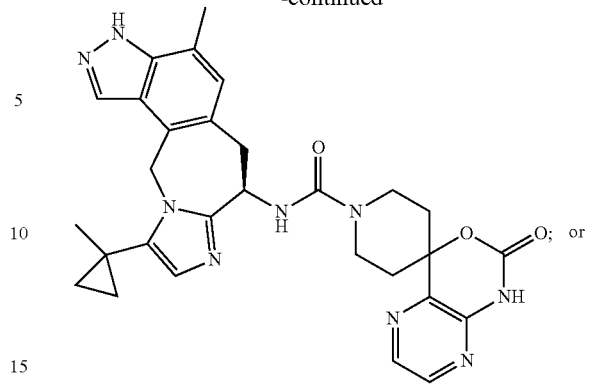

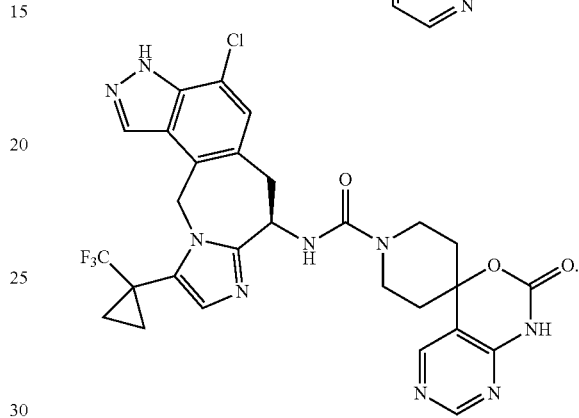

10. A pharmaceutical composition comprising an inert carrier and a compound of claim 1.

11. A method for treating headache in a mammalian patient in need of such comprising administering to the patient a therapeutically effective amount of a compound of claim 1, or individual stereoisomer thereof.

12. The method of claim 11, wherein said headache is migraine headache or cluster headache.

* * * * *